United States Patent
Patnala

(10) Patent No.: US 12,318,194 B2
(45) Date of Patent: Jun. 3, 2025

(54) SOUND DELIVERY APPARATUSES FOR AUDIOMETRIC MEASUREMENTS

(71) Applicant: Advanced Bionics AG, Staefa (CH)

(72) Inventor: Anil K. Patnala, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 1092 days.

(21) Appl. No.: 16/971,259

(22) PCT Filed: Feb. 27, 2018

(86) PCT No.: PCT/US2018/020016
§ 371 (c)(1),
(2) Date: Aug. 19, 2020

(87) PCT Pub. No.: WO2019/168504
PCT Pub. Date: Sep. 6, 2019

(65) Prior Publication Data
US 2020/0383613 A1    Dec. 10, 2020

(51) Int. Cl.
*A61B 5/12* (2006.01)
*A61N 1/36* (2006.01)
(Continued)

(52) U.S. Cl.
CPC .......... *A61B 5/125* (2013.01); *A61N 1/36038* (2017.08); *A61N 1/3758* (2013.01); *H04R 1/1016* (2013.01)

(58) Field of Classification Search
CPC ..... A61B 5/125; A61B 5/121; A61B 1/36038; A61B 1/3758; H04R 1/1016; H04R 25/70
See application file for complete search history.

(56) References Cited

U.S. PATENT DOCUMENTS

| 4,677,679 A | 6/1987 | Killion |
| 7,424,124 B2 | 9/2008 | Shennib et al. |
(Continued)

FOREIGN PATENT DOCUMENTS

WO    1999039548    8/1999

OTHER PUBLICATIONS

International Search Report and Written Opinion received in International Application No. PCT/US18/020016, dated Jun. 14, 2018.
(Continued)

*Primary Examiner* — Jennifer Bahls
*Assistant Examiner* — Quang X Nguyen
(74) *Attorney, Agent, or Firm* — ALG Intellectual Property, LLC

(57) ABSTRACT

An exemplary apparatus includes tubing that physically couples to an acoustic stimulation generator generating sound waves representative of acoustic stimulation used to obtain an audiometric measurement with respect to a patient. The tubing provides a first portion of a sound propagation channel from the acoustic stimulation generator to an ear canal of the patient. The apparatus further includes an ear tip disposed at the ear canal and including an external portion and an internal portion that couples to the tubing to provide a second portion of the sound propagation channel. The apparatus also includes a permanent bend associated with a coupling between the tubing and the ear tip. The permanent bend is disposed immediately outside the ear canal of the patient so as to angle the tubing toward a pinna of the patient without obstructing the sound propagation channel. Systems employing this exemplary apparatus are also disclosed.

20 Claims, 11 Drawing Sheets

(51) Int. Cl.
*A61N 1/375* (2006.01)
*H04R 1/10* (2006.01)

(56) References Cited

U.S. PATENT DOCUMENTS

| | | | |
|---|---|---|---|
| 8,103,031 B2 | 1/2012 | Ho et al. | |
| 9,118,995 B1 | 8/2015 | Feeley et al. | |
| 9,473,843 B2 | 10/2016 | Rasmussen et al. | |
| 2004/0165742 A1 | 8/2004 | Shennib et al. | |
| 2007/0009107 A1 | 1/2007 | Lange | |
| 2009/0092271 A1 | 4/2009 | Fay et al. | |
| 2009/0190786 A1 | 7/2009 | Miskiel et al. | |
| 2009/0202097 A1* | 8/2009 | Tiscareno | H04R 1/1016 381/380 |
| 2010/0316225 A1 | 12/2010 | Saito et al. | |
| 2011/0036661 A1* | 2/2011 | Munro | A61F 11/08 181/135 |
| 2011/0116669 A1 | 5/2011 | Karunasiri | |
| 2011/0176700 A1 | 7/2011 | Hashimoto | |
| 2011/0216927 A1 | 9/2011 | Ball | |
| 2012/0087511 A1* | 4/2012 | Lumsden | H04R 1/1083 381/74 |
| 2012/0300964 A1 | 11/2012 | Ku et al. | |
| 2013/0056295 A1 | 3/2013 | Campbell et al. | |
| 2014/0193022 A1 | 7/2014 | Koizumi | |
| 2015/0237451 A1 | 8/2015 | Launer | |
| 2016/0015033 A1 | 5/2016 | Wenzel | |
| 2016/0173971 A1* | 6/2016 | Lott | H04R 25/652 381/380 |
| 2016/0235986 A1 | 8/2016 | Murad et al. | |
| 2016/0373868 A1 | 12/2016 | Karamuk et al. | |
| 2017/0095372 A1 | 4/2017 | Aceti et al. | |
| 2019/0208303 A1* | 7/2019 | Monti | H04R 25/656 |

OTHER PUBLICATIONS

Phonak Technical Data—Lyric 3, V1.30/2015-11/JrA Phonak AG.

* cited by examiner

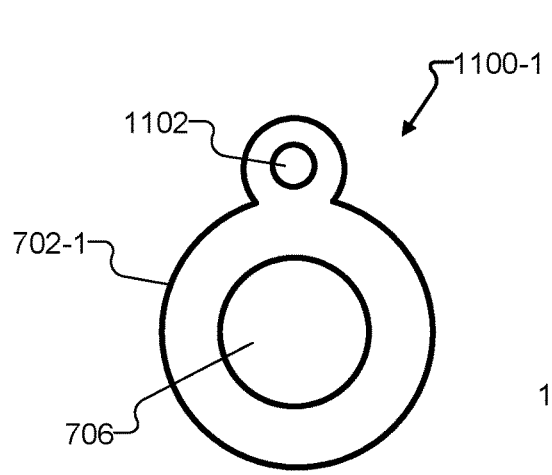
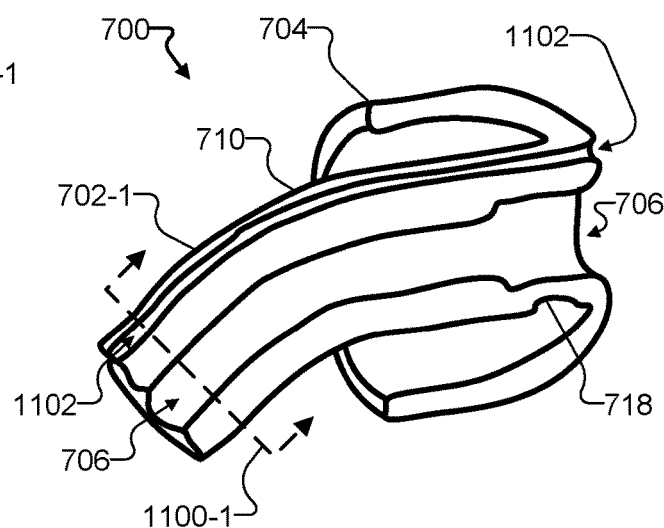
Fig. 11A  Fig. 11B
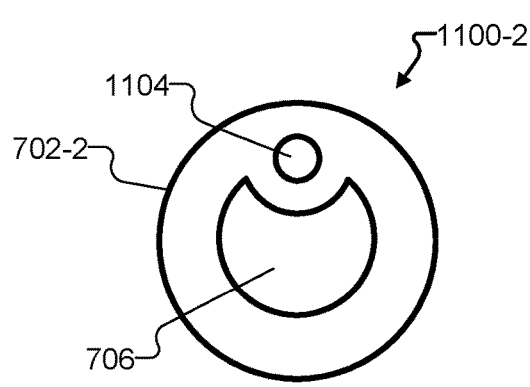
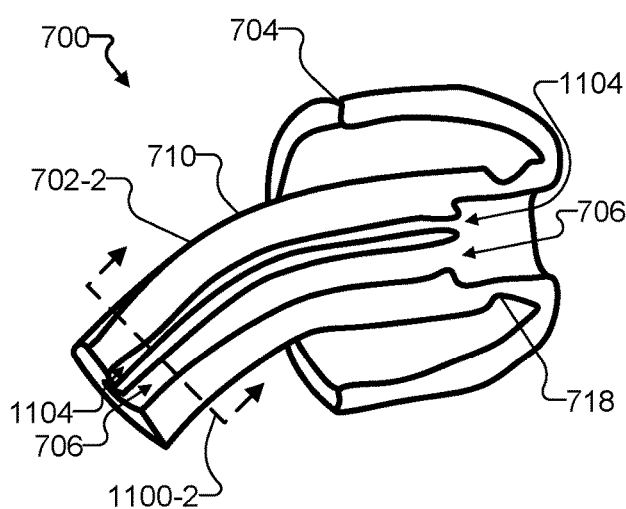
Fig. 11C  Fig. 11D

SOUND DELIVERY APPARATUSES FOR AUDIOMETRIC MEASUREMENTS

BACKGROUND INFORMATION

Cochlear implant systems are used to improve and/or restore hearing loss suffered by patients who use the cochlear implant systems. For example, a patient may be implanted with a cochlear implant configured to communicate with a sound processor and, under direction of the sound processor, to electrically stimulate different areas of cochlear tissue of the patient to thereby provide a sense of hearing to the patient.

During the lifetime of a cochlear implant system, it may be useful or necessary for various audiometric measurements to be obtained with respect to the patient associated with the cochlear implant system. For example, audiometric measurements may include or be associated with any of various tests, assessments, analyses, or the like, in which acoustic stimulation is presented to a patient and an evoked response (e.g., a voluntary or involuntary evoked response) to the stimulation is measured.

Regardless of the purpose for or nature of a particular audiometric measurement, it may be desirable for the acoustic stimulation associated with the audiometric measurement to be delivered and presented to the patient in a controlled, precise, and convenient manner.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 11A-11D illustrate cross sectional views of exemplary implementations of the ear tip of FIG. 7 that are configured to facilitate monitoring, within an ear canal of a patient, acoustic stimulation used to obtain an audiometric measurement with respect to the patient according to principles described herein.

DETAILED DESCRIPTION

Figure 1:
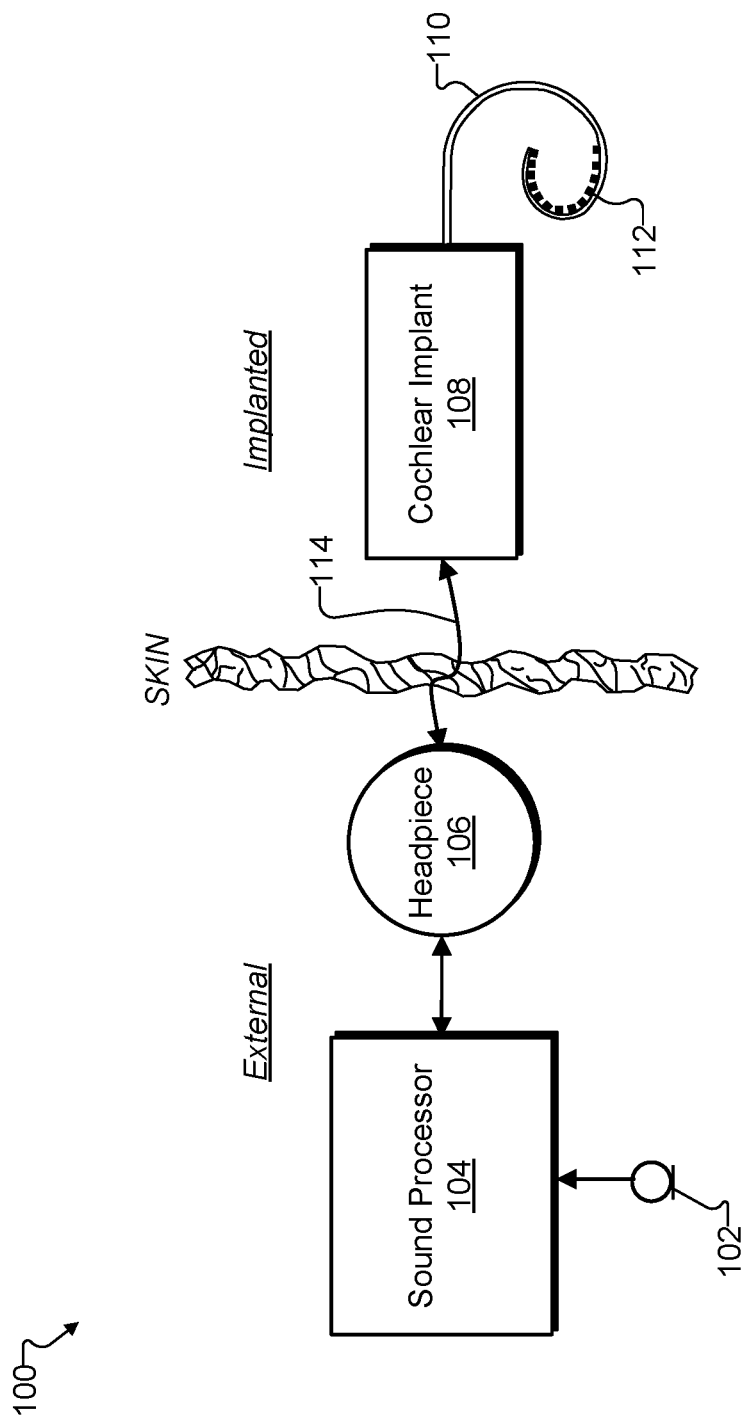
FIG. 1 illustrates an exemplary cochlear implant system according to principles described herein.

Sound delivery apparatuses for audiometric measurements are described herein. For example, a sound delivery apparatus such as the sound delivery apparatuses described herein may be employed when obtaining audiometric measurements with respect to a patient during a surgical operation associated with a cochlea of the patient (e.g., an insertion procedure by way of which an electrode lead is surgically implanted into the cochlea). In other examples, the sound delivery apparatus may be employed during a fitting procedure by way of which an audiologist optimizes and customizes operation of a cochlear implant system to the patient, as part of an effort to diagnose and/or troubleshoot problems with the cochlear implant system, and/or at other times during a period of time in which the patient uses the cochlear implant system.

In certain implementations, a sound delivery apparatus may include a length of tubing configured to physically couple (e.g., at a proximal end of the tubing) to an acoustic stimulation generator configured to generate sound waves representative of acoustic stimulation used to obtain an audiometric measurement with respect to a patient. The tubing may provide a first portion of a sound propagation channel that extends from the acoustic stimulation generator (e.g., where the sound waves representative of the acoustic stimulation are generated) to an ear canal of the patient (e.g., where the sound waves are to be delivered for the audiometric measurement to be successfully obtained).

The sound delivery apparatus may further include an ear tip configured to be disposed at the ear canal of the patient. The ear tip may include an external portion configured to interface with the ear canal of the patient (e.g., a dome-shaped or other suitably shaped portion constructed of a soft material so as to fit comfortably and to form an isolated seal in the ear canal of the patient). The ear tip may further include an internal portion configured to be coupled to a distal end of the tubing (i.e., an opposite end from the proximal end of the tubing physically coupled to the acoustic stimulation generator). The internal portion may be formed in a tubular shape similar to the tubing so as to provide, when coupled to the tubing, a second portion of the sound propagation channel that extends from the acoustic stimulation generator to the ear canal of the patient.

The sound delivery apparatus may further include a permanent bend associated with a coupling between the distal end of the tubing and the internal portion of the ear tip. For example, the permanent bend may be associated with the coupling by being disposed on the distal end of the tubing near where the distal end of the tubing is coupled to the internal portion of the ear tip, on the internal portion of the ear tip near where internal portion is coupled to the distal end of the tubing, on a coupling adapter by way of which the distal end of the tubing is coupled to the internal portion of the ear tip, on each of a plurality of these components, and/or in another suitable location associated with the coupling. Regardless of which component or components of the sound delivery apparatus include the permanent bend, the permanent bend may be configured to be disposed immediately outside the ear canal of the patient when the ear tip is disposed at the ear canal and coupled to the distal end of the tubing. As such, when the sound delivery apparatus is properly assembled and put in place on the patient for an audiometric measurement to be obtained, the permanent bend may angle the tubing toward a pinna of the patient (e.g., in any direction toward the cartilage of the outer ear) without obstructing the sound propagation channel such as by pinching or kinking the sound propagation channel to be at least partially closed off or otherwise obstructed.

In some examples, a sound delivery apparatus such as described herein may be included as part of an audiometric measurement system and used to deliver acoustic stimulation for a particular audiometric measurement. For instance, the audiometric measurement system (e.g., an acoustic stimulation generator included within the audiometric measurement system) may generate acoustic stimulation to be delivered to a patient by way of the sound delivery apparatus to thereby elicit an evoked response that may be detected by the audiometric measurement system. The evoked response may be any type of evoked response as may serve a particular implementation. For example, as used herein, an "evoked response" associated with an audiometric measurement may refer to a voluntarily generated response such as verbal feedback provided by the patient to describe how the patient perceives the generated acoustic stimulation. For instance, verbally articulated explanations of a patient's perceptions may be used to determine the patient's ability to discriminate between different sound intensities, to recognize pitch, to distinguish speech from background noise, and so forth. In other examples, an "evoked response," as used herein, may refer to a response generated by the patient involuntarily (e.g., by way of an automatic physiological response) so as to indicate information of which the patient may not be consciously aware and/or able to verbally articulate. For example, the evoked response may be an electrocochleographic ("ECoG") potential (e.g., a cochlear microphonic potential, an action potential, a summating potential, etc.), an auditory nerve response, a brainstem response, a compound action potential, and/or any other type of neural or physiological response that may occur within a patient in response to application of the acoustic stimulation to the patient. In some examples, evoked responses may originate from neural tissues, hair cell to neural synapses, inner or outer hair cells, or other sources.

In certain examples, the audiometric measurement system in which the sound delivery apparatus is included may be implemented more particularly as an intraoperative audiometric measurement system, also referred to herein as an intraoperative measurement system. The intraoperative measurement system may include various components used to obtain an audiometric measurement intraoperatively, or, in other words, in real time while a surgical operation (e.g., a lead insertion procedure or other operation associated with a cochlea of the patient) is being performed on the patient.

For example, the intraoperative measurement system may include a probative electrode disposed on an electrode lead included within a cochlear implant system and that is being inserted into a cochlea of a patient during a surgical operation. The probative electrode may be configured to detect (e.g., while the probative electrode is positioned at a particular location within the cochlea of the patient) an evoked response that occurs in response to acoustic stimulation applied to the patient. The intraoperative measurement system may further include an acoustic stimulation generator configured to generate sound waves representative of the acoustic stimulation.

Additionally, the intraoperative measurement system may include a sound delivery apparatus such as described above to provide a sound propagation channel capable of delivering the acoustic stimulation without interfering with the surgical operation or becoming dislodged or obstructed when, for example, a surgeon performing the surgical operation bumps the tubing or moves the tubing out of the way during the operation. Specifically, similar to the sound delivery apparatus described above, the sound delivery apparatus included within the intraoperative measurement system may include 1) a length of tubing configured to physically couple (e.g., at a proximal end of the tubing) to the acoustic stimulation generator and to provide a first portion of a sound propagation channel from the acoustic stimulation generator to an ear canal of the patient; 2) an ear tip configured to be disposed at the ear canal of the patient while the patient is undergoing the surgical operation, the ear tip including an external portion configured to interface with the ear canal of the patient and an internal portion configured to be coupled to a distal end of the tubing to provide a second portion of the sound propagation channel; and 3) a permanent bend associated with a coupling between the distal end of the tubing and the internal portion of the ear tip, the permanent bend configured to be disposed immediately outside the ear canal of the patient so as to angle the tubing toward a pinna of the patient without obstructing the sound propagation channel when the ear tip is disposed at the ear canal and coupled to the distal end of the tubing as the patient is undergoing the surgical operation.

Sound delivery apparatuses for audiometric measurements disclosed herein may provide various benefits as compared to conventional sound delivery apparatuses used to obtain audiometric measurements on patients. For example, while intraoperative audiometric measurements may provide surgical insight and guidance helpful to surgeons and/or other people assisting in a surgical operation, conventional sound delivery apparatuses that come straight out from the patient's ear canal (e.g., at an angle approximately parallel to the ear canal, rather than being angled down toward the pinna of the patient) may interfere with the surgical operation such as by obstructing a clear view of the operation area, by physically getting in the way of the surgeon or others, or in other similar ways.

Additionally, and as a consequence of the interference of conventional sound delivery apparatuses during surgery, actions taken by the surgeon or others during an operation may cause ear tips of conventional sound delivery apparatuses to be inadvertently bumped and/or dislodged. Alternatively, to attempt to avoid such inadvertent interference, a surgical team may attempt to keep a conventional sound delivery apparatus from interfering with the surgical operation by folding and taping down the pinna of the patient to keep the tubing out of the way and/or to prevent fluids associated with the operation from reaching the ear canal. However, while bending tubing in this way may alleviate problems associated with interference from the tubing, bending straight tubing may create additional problems. For instance, by bending this tubing and/or taping it down to be out of the way, the tubing of a conventional sound delivery apparatus may become kinked, pinched shut, or otherwise obstructed. Additionally, this bending may place strain on the ear tip, which may cause the ear tip to become displaced or dislodged from an optimal position at the ear canal.

Unfortunately, any of these types of obstructions, displacements, and/or dislodgements of the components of the sound delivery apparatus may create significant problems and/or inconveniences during surgery. For example, in certain intraoperative circumstances, it may be difficult, impractical, or impossible to unobstruct and/or to reinsert and properly place sound delivery apparatuses that become intraoperatively obstructed, displaced, or dislodged. As a result, if such obstruction, displacement, or dislodgement of the sound delivery apparatus occurs, all the benefits provided by the intraoperative audiometric measurements may be lost for a duration of the surgical operation. Additionally, such obstructions, displacements, and/or dislodgements may lead to inaccurate or undesirable measurement results. For example, certain audiometric measurements may require a high degree of precision in the acoustic stimulation that is delivered to the patient and may be inaccurate when a propagation channel for the acoustic stimulation is even partially obstructed from the causes described above.

Consequently, sound delivery apparatuses for audiometric measurements described herein may benefit patients and people obtaining audiometric measurements, performing surgery, etc., by helping ensure that audiometric measurements are obtained accurately, effectively, and conveniently. For example, sound delivery apparatuses described herein may inherently be configured to have a lower risk of interfering with a surgery or being obstructed, displaced, dislodged, or otherwise negatively affected as compared to conventional sound delivery apparatuses.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. For example, sound delivery apparatuses described herein may be used to obtain audiometric measurements during surgical operations by way of which a cochlear implant system such as cochlear implant system 100 is outfitted onto and/or implanted within a patient. As another example, sound delivery apparatuses described herein may be used to obtain audiometric measurements for fitting, troubleshooting, or otherwise maintaining and using cochlear implant system 100 during the period of time that the patient uses the cochlear implant system. As such, cochlear implant system 100 will be described below as cochlear implant system 100 functions in normal operation, although it will be understood that certain aspects of the normal operation of cochlear implant system 100 described herein may not apply while audiometric measurements are being obtained (e.g., while tests associated with the audiometric measurements are being performed).

As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into a cochlea of a patient to stimulate the cochlea when the distal portion of electrode lead 110 is inserted into the cochlea. One or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

During normal operation, sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a CPI device, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108.

When an audiometric measurement is being obtained, sound processor 104 may operate in a probative mode of operation (e.g., a mode different from normal operation). In this mode, for example, sound processor 104 may not direct electrical stimulation to be applied to the patient but, rather, may direct lead 110 and electrodes 112 to be used to detect evoked responses that are generated by the patient in response to acoustic stimulation. For example, as will be described in more detail below, sound processor 104 may direct cochlear implant 108 to use lead 110 and electrodes 112 to measure voltages, currents, impedances, or other characteristics within the cochlea representative of the evoked responses to the acoustic stimulation. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bidirectional communication link and/or one or more dedicated unidirectional communication links as may serve a particular implementation).

Cochlear implant 108 may include any suitable type of implantable stimulator. For example, cochlear implant 108 may be implemented by an implantable cochlear stimulator. Additionally or alternatively, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
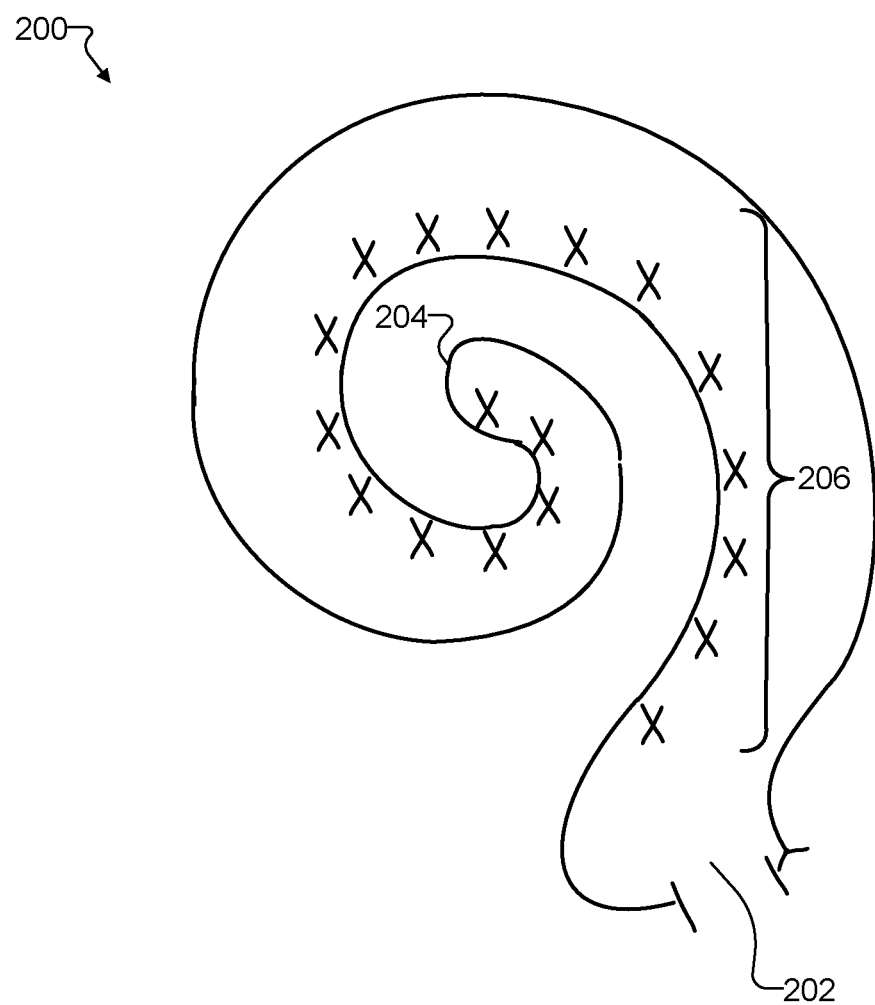
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

Figure 3:
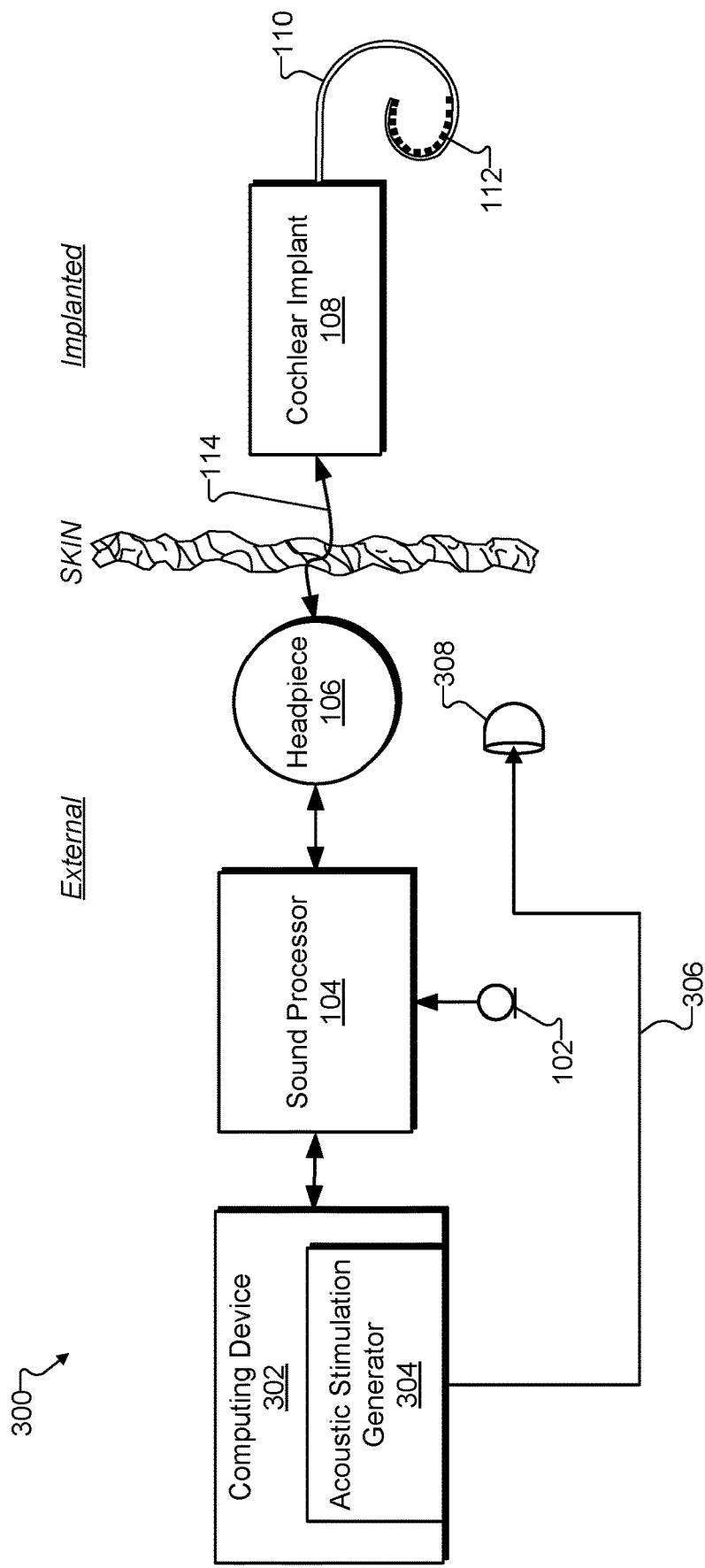
FIG. 3 illustrates an exemplary audiometric measurement system in which a computing device is communicatively coupled to the cochlear implant system of FIG. 1 according to principles described herein.

In some examples, cochlear implant system 100, described above, may be included within an audiometric measurement system used to obtain audiometric measurements with respect to a patient associated with cochlear implant system 100. To illustrate, FIG. 3 shows an exemplary audiometric measurement system 300 in which a computing device 302 is communicatively coupled to cochlear implant system 100 (e.g., to sound processor 104, in particular). Computing device 302 may be implemented by any suitable combination of physical computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation.

In some examples, computing device 302 may provide one or more user interfaces with which a user may interact. For example, a user interface may provide text, graphics, sounds, etc., to facilitate a successful insertion procedure of electrode lead 110 (e.g., by facilitating audiometric measurements) or effective programming of sound processor 104 as may serve a particular implementation. In some implementations, the user interface provided by computing device 302 may include a graphical user interface ("GUI") that allows a user (e.g., a surgeon, a person assisting the surgeon intraoperatively, a clinician in a non-intraoperative situation, etc.) to direct computing device 302 to perform operations used to obtain an audiometric measurement, to view or hear results of the audiometric measurement, or the like.

To this end, as shown, computing device 302 may include an acoustic stimulation generator 304. While illustrated as being included within computing device 302, it will be understood that, in certain examples, acoustic stimulation generator 304 may be a separate device from computing device 302, such as a device that is communicatively coupled with and controlled by computing device 302. As further shown, a sound propagation channel 306 may extend from acoustic stimulation generator 304 to an ear tip 308 so as to carry acoustic stimulation (e.g., sound) generated by acoustic stimulation generator 304 to ear tip 308, which may be disposed at an ear canal of the patient associated with cochlear implant system 100.

In operation, audiometric measurement system 300 may perform many or all of the types of operations described above in relation to cochlear implant system 100. However, audiometric measurement system 300 may further provide acoustic stimulation to the patient so as to thereby obtain audiometric measurements with respect to the patient in accordance with techniques described herein or other suitable techniques used to obtain audiometric measurements.

Specifically, for example, computing device 302 may direct acoustic stimulation generator 304 to generate acoustic stimulation to be carried by sound propagation channel 306 to be presented at the ear canal of the patient through ear tip 308. In certain examples, cochlear implant system 100 may be fully installed and undergoing normal operation (e.g., applying electrical stimulation to the cochlea of the patient based on an audio signal detected by microphone 102) as computing device 302 directs the obtaining of the audiometric measurement. For instance, for an audiometric measurement in which a voluntary evoked response (e.g., verbal feedback) is provided by the patient rather than an involuntarily evoked response, computing device 302 may direct acoustic stimulation generator 304 to generate the acoustic stimulation to be carried by sound propagation channel 306 to ear tip 308 while cochlear implant system 100 operates normally or is switched off for the test.

In other examples, however, computing device 302 may direct acoustic stimulation generator 304 to present acoustic stimulation to the patient (e.g., by way of sound propagation channel 306 and ear tip 308) while also directing cochlear implant system 100 to detect an involuntary evoked response to the presented acoustic stimulation. Specifically, as the acoustic stimulation is presented at the ear canal of the patient, computing device 302 may instruct sound processor 104 to direct cochlear implant 108 (e.g., transcutaneously by way of headpiece 106 and communication link 114) to detect an involuntary evoked response (e.g., an ECoG response or the like) by way of one or more electrodes 112 on lead 110. Thus, as mentioned above, cochlear implant system 100 may operate in a probative mode (e.g., rather than according to normal operation) as such audiometric measurements are obtained, such that microphone 102 may not be used, and cochlear implant 108, lead 110, and electrodes 112 may be used to detect one or more evoked responses rather than to apply electrical stimulation, and so forth.

Additionally, in some examples, cochlear implant system 100 may not be fully installed when audiometric measurement system 300 is obtaining an audiometric measurement. Rather, implantable components of cochlear implant system 100 may be in the process of being implanted when the audiometric measurement is obtained. For example, audiometric measurement system 300 may act as an intraoperative measurement system that is configured to obtain audiometric measurements during a surgical insertion procedure of lead 110 (including electrodes 112) into the cochlea of the patient.

Because lead insertion procedures are delicate and difficult procedures that have a potential to result in cochlear trauma or other harm if not done with extreme care, surgeons and other people involved in insertion procedures may desire to carefully monitor and track the electrode lead by identifying its position and insertion path with respect to the cochlea during and after the insertion procedure. It may also be desirable to detect any trauma that may occur to the cochlea as a result of an insertion procedure. Fortunately, obtaining audiometric measurements using the sound delivery apparatuses for audiometric measurements described herein may facilitate detecting trauma and identifying the position and/or insertion path of an electrode lead within a patient without having to resort to expensive, risky, or inconvenient image technologies such as x-ray technology, fluoroscopic technology, CT scanning technology, or the like. For example, audiometric measurements may help detect scalar translocations of the lead being inserted.

As used herein, a "scalar translocation" of an electrode lead refers to a translocation (i.e., a movement from one location to another) of an electrode lead (e.g., a distal end of the electrode lead, in particular) from one scala of the cochlea of a patient (e.g., the scala tympani) to another scala of the cochlea of the patient (e.g., the scala vestibuli). For example, during an insertion procedure whereby an electrode lead is inserted into a cochlea, the electrode lead may travel through the round window into the scala tympani of the cochlea but, instead of continuing to travel through the scala tympani, may inadvertently puncture the basilar membrane and/or other anatomy separating the scala tympani from the scala vestibuli to enter the scala vestibuli. Because such a scalar translocation may damage the basilar membrane (e.g., including hair cells disposed on the basilar membrane and associated with residual hearing of the patient), the translocation of the electrode lead may cause trauma to the cochlea. As such, it may be desirable to detect scalar translocation in real time during the insertion procedure (e.g., so that the scalar translocation may be corrected if possible) and/or after the fact (e.g., so that the scalar translocation may be associated with data being studied to help reduce trauma and improve outcomes in subsequent insertion procedures).

Figure 4:
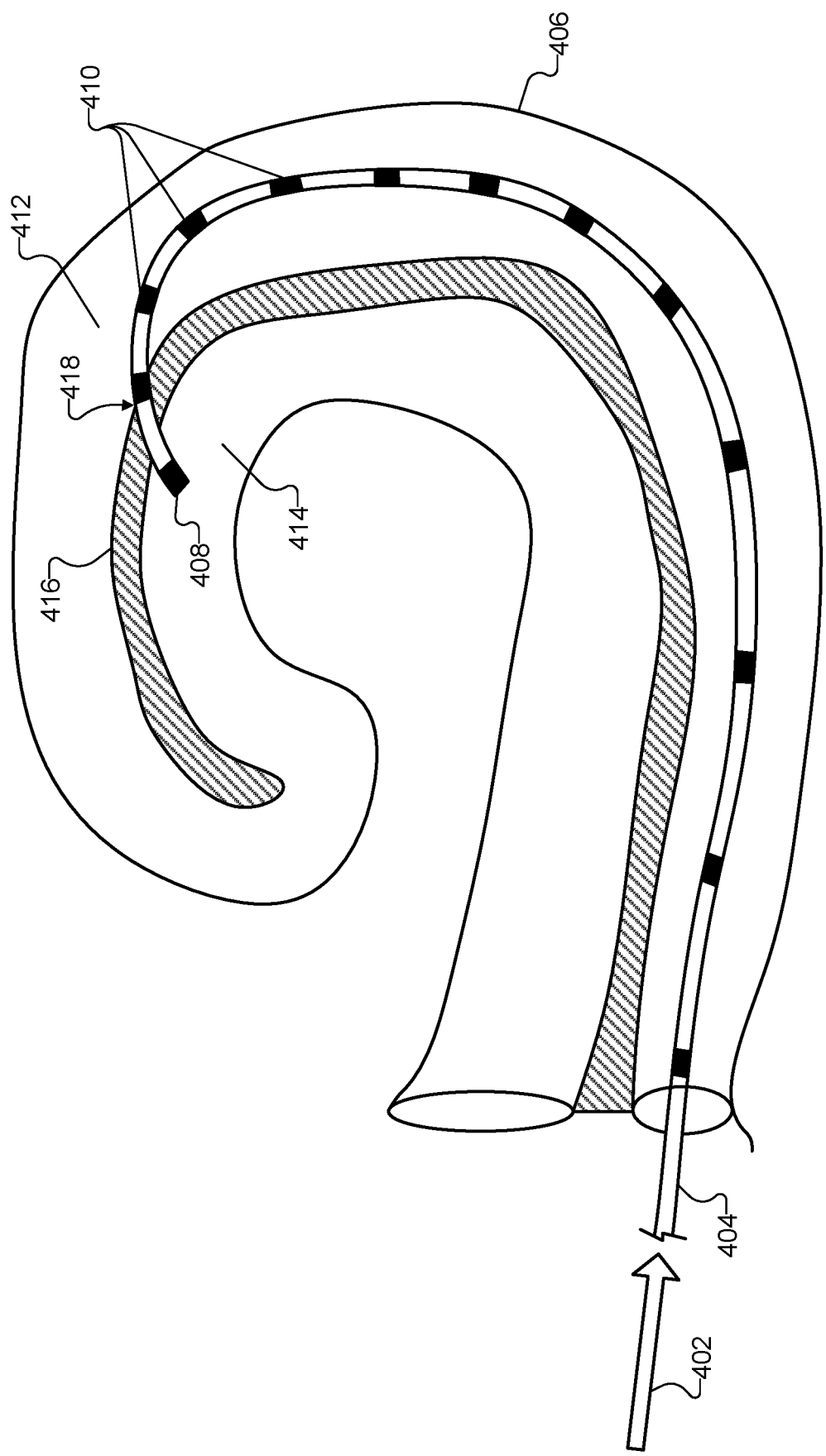
FIG. 4 illustrates exemplary aspects of an electrode lead and of patient anatomy as an exemplary insertion procedure is performed according to principles described herein.

To illustrate, FIG. 4 shows exemplary aspects of an electrode lead and of patient anatomy as an exemplary insertion procedure is performed on the patient. Specifically, as shown, an insertion procedure 402 is illustrated in which a distal portion of an electrode lead 404 is inserted into a cochlea 406 of a patient. It will be understood that, while only a distal portion of electrode lead 404 is illustrated in FIG. 4, a proximal portion of the electrode lead not explicitly shown may be coupled to a cochlear implant (also not shown) that may direct current into electrode lead 404, receive and pass on data detected by electrode lead 404 (e.g., evoked response data or the like), and so forth, as described above with respect to lead 110 and cochlear implant 108.

As shown, electrode lead 404 may include various electrodes including a probative (e.g., leading) electrode 408 nearest a distal end of electrode lead 404 and several additional electrodes 410 disposed along the length of electrode lead 404. While the leading electrode (i.e., electrode 408) is referred to herein as the probative electrode, it will be understood that any of electrodes 410 may serve as the probative electrode (or as one of a plurality of probative electrodes) as may serve a particular implementation.

As illustrated in FIG. 4, insertion procedure 402 may involve inserting electrode lead 404 through a suitable location (e.g., a round window or cochleostomy of cochlea 406) and into a scala tympani 412 of cochlea 406. Scala tympani 412 is a chamber of cochlea 406 that is separated from a scala vestibuli 414 of cochlea 406 (i.e., a separate chamber of cochlea 406) by a basilar membrane 416 (e.g., as well as other membranes and anatomical structures not explicitly shown or labeled in FIG. 4).

FIG. 4 illustrates electrode lead 404 within cochlea 406 at a particular moment during insertion procedure 402. Specifically, at the moment depicted in FIG. 4, electrode lead 404 has translocated from scala tympani 412, through basilar membrane 416, and into scala vestibuli 414 at a translocation site 418. This scalar translocation of electrode lead 404 may have occurred for any of a variety of reasons during insertion procedure 402, but is most likely an undesirable occurrence because, as shown, the distal end of electrode lead 404 (i.e., at probative electrode 408) has physically penetrated basilar membrane 416, thereby potentially causing trauma to basilar membrane 416 and/or any of various other parts of cochlea 406 associated with basilar membrane 416 (e.g., previously functional hair cells along basilar membrane 416, other membranes or nerves associated with basilar membrane 416, etc.).

To mitigate trauma caused by the scalar translocation of electrode lead 404 and/or to facilitate avoidance of similar scalar translocations in future insertion procedures, audiometric measurements may be obtained to help detect the scalar translocations. Specifically, a scalar translocation of electrode lead 404 from scala tympani 412 to scala vestibuli 414 may be determined based on an amplitude change and/or a phase change between different audiometric measurements (e.g., different ECoG measurements) obtained at different points in time (e.g., and, thus, at different insertion depths) during insertion procedure 402. Information representative of such a detected scalar translocation may be provided to inform a surgical team that electrode lead 404 should be backed out and reinserted to try to avoid the scalar translocation prior to completing insertion procedure 402, or may be stored or otherwise used as may serve a particular implementation.

Regardless of whether audiometric measurements are obtained intraoperatively by system 300 for a procedure such as insertion procedure 402 or are obtained non-intraoperatively, it may be beneficial for a sound delivery apparatus to have certain characteristics. For example, various benefits described herein may result from a sound delivery apparatus that is resistant to kinking, that is configured to avoid interfering with a surgical procedure (e.g., an insertion procedure such as insertion procedure 402), that provides an unobstructed sound propagation channel and maximum isolation for sound presented at the ear canal, and so forth. To this end, various implementations of sound delivery apparatuses that have these and/or other beneficial characteristics will now be described.

Figure 5:
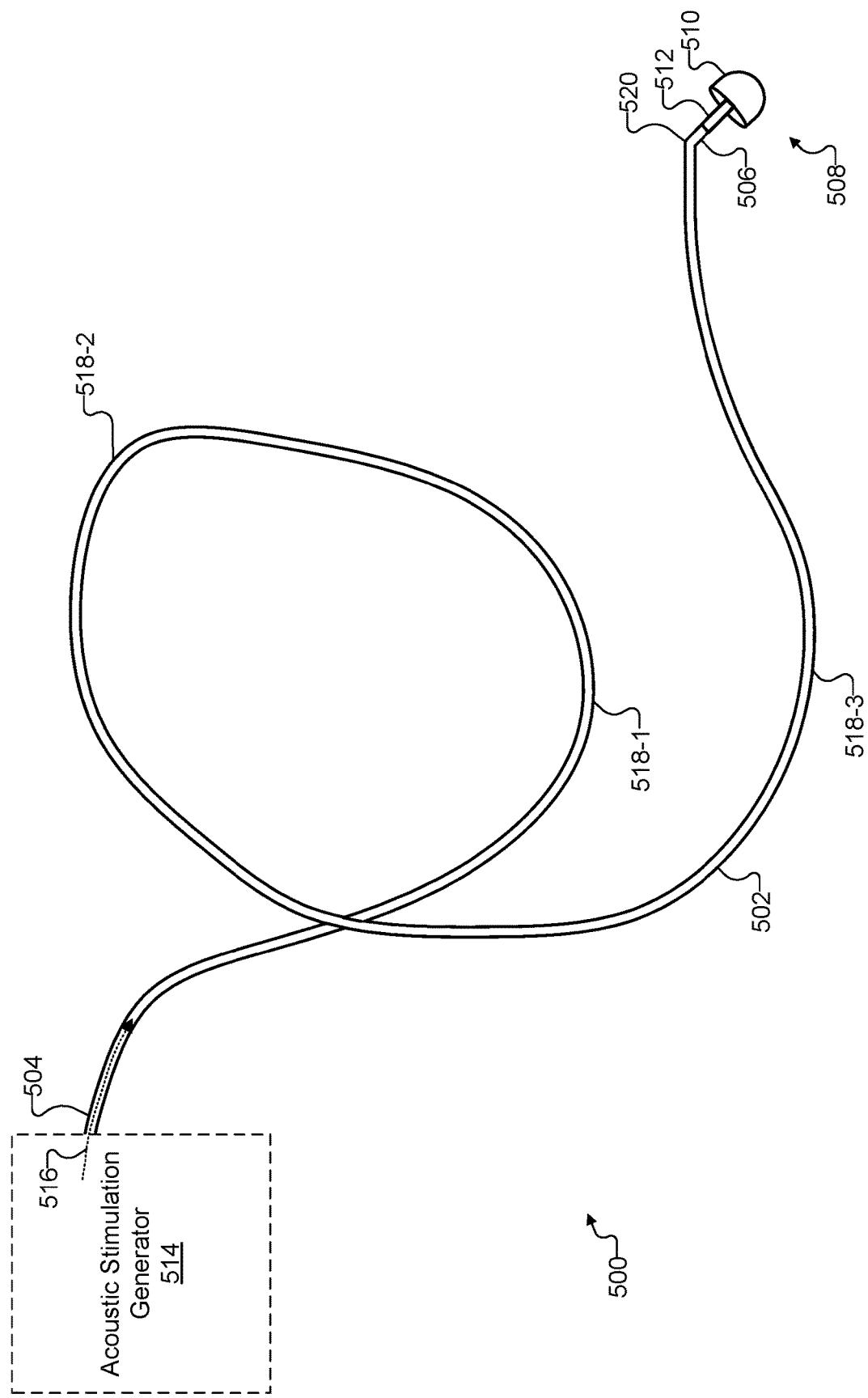
FIG. 5 illustrates an exemplary sound delivery apparatus for audiometric measurements that is configured to deliver acoustic stimulation from an exemplary acoustic stimulation generator to an ear canal of a patient according to principles described herein.

FIG. 5 illustrates an exemplary sound delivery apparatus 500 for audiometric measurements that is configured to deliver acoustic stimulation from an exemplary acoustic stimulation generator to an ear canal of a patient. Specifically, as depicted in FIG. 5, sound delivery apparatus 500 may include a length of tubing 502 that includes a proximal end 504 and a distal end 506. Sound delivery apparatus 500 may further include an ear tip 508 that is configured to be disposed at the ear canal of a patient. Ear tip 508 may include an external portion 510 configured to interface with the ear canal of the patient, as well as an internal portion 512 configured to be coupled to distal end 506 of tubing 502.

When assembled (e.g., when tubing 502 is physically coupled with ear tip 508), sound delivery apparatus 500 may be coupled to an acoustic stimulation generator 514 (e.g., similar or identical to acoustic stimulation generator 304, described above) so as to provide a sound propagation channel 516 from acoustic stimulation generator 514 to the ear canal of the patient where ear tip 508 is disposed. Specifically, acoustic stimulation generator 514 may be configured to generate sound waves representative of acoustic stimulation used to obtain an audiometric measurement with respect to a patient in a similar or identical way as acoustic stimulation generator 304, described above, and tubing 502 may be configured to physically couple, at proximal end 504, to acoustic stimulation generator 514. In this way, tubing 502 may provide a first portion of sound propagation channel 516 from acoustic stimulation generator 514 to the ear canal, while internal portion 512 of ear tip 508, which is coupled to tubing 502 at distal end 506, may provide a second portion of sound propagation channel 516 that goes the rest of the way to the ear canal when ear tip 508 is disposed at the ear canal.

As further illustrated in FIG. 5, sound delivery apparatus 500 may include one or more bends 518 (e.g., bends 518-1 through 518-3) that may move and change as sound delivery apparatus 500 is positioned in place on the patient and moved and adjusted as one or more audiometric measurements are obtained. Bends 518 may occur naturally as a result of a flexibility of tubing 502, which may be constructed of a flexible material that allows for low impact bends (i.e., bends that are relatively loose or have a relatively large radius of curvature) as may be convenient for the patient and/or someone obtaining an audiometric measurement (e.g., a surgeon performing an insertion procedure, etc.). However, as described above, it may be undesirable for tubing 502 to be bent with a relatively tight turn (e.g., a bend with a relatively small radius of curvature) because tubing 502 may be kinked, pinched shut, or otherwise obstructed to compromise the integrity of sound propagation channel 516. At the same time, however, a relatively abrupt or tight turn of tubing 502 may be desirable near the ear canal so as to, for example, prevent tubing 502 from interfering with a surgeon performing a delicate procedure near the ear canal.

Accordingly, along with temporary bends 518 that may naturally result within tubing 502, sound delivery apparatus 500 may further include a permanent bend 520 that is associated with a coupling between distal end 506 of tubing 502 and internal portion 512 of ear tip 508. For example, as shown, permanent bend 520 may be configured to be disposed immediately outside the ear canal of the patient (e.g., implemented on tubing 502, on internal portion 512, on another member through which sound propagation channel 516 passes near the coupling between distal end 506 and internal portion 512, or on a combination thereof). In this way, permanent bend 520 may angle tubing 502 toward a pinna of the patient (e.g., toward an outer edge of the ear rather than coming straight out of the ear canal) without obstructing sound propagation channel 516 when ear tip 508 is disposed at the ear canal and coupled to distal end 506 of tubing 502. As such, for example, permanent bend 520 may angle tubing 502 toward the pinna as the patient is undergoing a surgical operation so as to reduce an interaction that a surgeon performing the surgical operation has with the tubing.

Various features of the components comprised within sound delivery apparatus 500 (e.g., ear tip 508, tubing 502, etc.) will be described below in conjunction with different embodiments where permanent bend 520 is implemented in different ways or disposed on different components. It will be understood, however, that any features described herein for any ear tip or tubing may be employed in any embodiment of sound delivery apparatus 500 as may serve a particular implementation. Additionally, it will be understood that components having the features described herein may be constructed of different materials, in different sizes, and with different features appropriate for various types of patients (e.g., pediatric patients, geriatric patients, etc.).

As mentioned above, in some examples, an audiometric measurement that is obtained using a sound delivery apparatus such as sound delivery apparatus 500 may be an intraoperative audiometric measurement performed as the patient is undergoing a surgical operation associated with a cochlea of the patient (e.g., a lead insertion procedure or the like). Accordingly, sound delivery apparatus 500 may, in such examples, be used as part of an audiometric measurement system, and, more particularly, as part of an intraoperative measurement system. For example, the intraoperative measurement system may include an implementation of sound delivery apparatus 500, as well as, for example, an acoustic stimulation generator such as acoustic stimulation generator 514 and a probative electrode disposed on an electrode lead included within a cochlear implant system such as illustrated and described above (see, e.g., probative electrode 408 on electrode lead 404, one of electrodes 112 on lead 110 in cochlear implant system 100, etc.). For instance, the probative electrode may be configured to detect (e.g., while the probative electrode is positioned at a particular location within a cochlea of a patient who is undergoing a surgical operation associated with the cochlea) an evoked response that occurs in response to acoustic stimulation applied to the patient by acoustic stimulation generator 514 through the sound propagation channel 516 provided by sound delivery apparatus 500.

Figure 6:
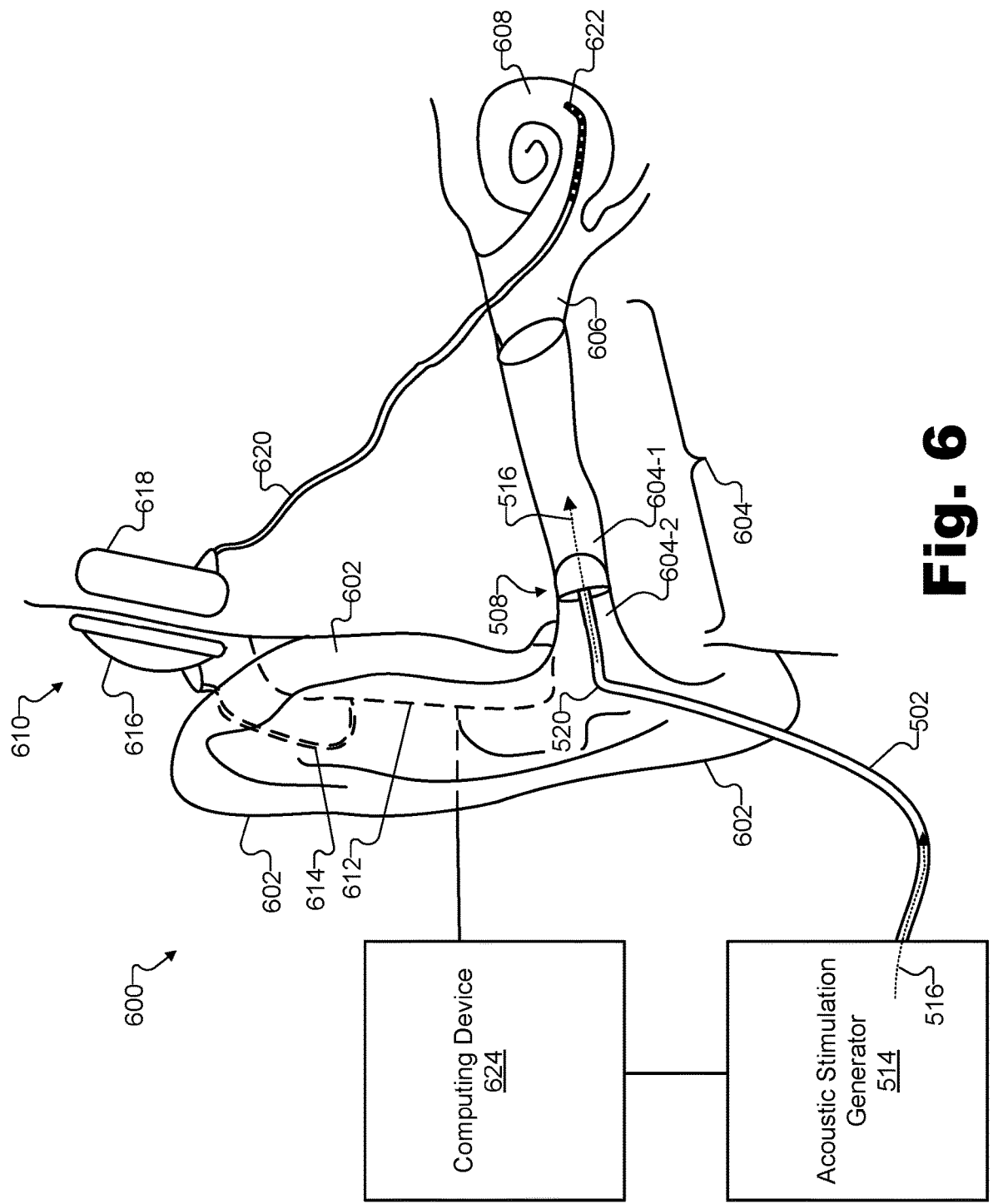
FIG. 6 illustrates an exemplary configuration in which the sound delivery apparatus of FIG. 5 operates within an exemplary intraoperative measurement system used to obtain intraoperative audiometric measurements with respect to a patient according to principles described herein.

To illustrate such an intraoperative measurement system in operation during a surgical operation, FIG. 6 depicts an exemplary configuration in which sound delivery apparatus 500 is operating within an exemplary intraoperative measurement system 600 used to obtain intraoperative audiometric measurements with respect to a patient undergoing a surgical operation associated with the cochlea of the patient (e.g., an electrode lead insertion procedure such as insertion procedure 402). Specifically, as shown in FIG. 6, the anatomy of an ear of a patient includes a pinna 602 (i.e., the outer ear), an ear canal 604 having an interior part 604-1 and an exterior part 604-2, a middle ear 606, and a cochlea 608. While no specific incision or other explicit surgical representation is shown in FIG. 6, it will be understood that such elements may be present when a surgical operation is ongoing. For example, an incision may be present to allow the surgeon internal access to the patient to insert the lead into cochlea 608, pinna 602 may be taped down so as to cover ear canal 604 (e.g., to help prevent fluids associated with the operation from reaching ear canal 604), and so forth.

A cochlear implant system 610 is shown to be integrated with and at least partially implanted within the patient. Specifically, as shown, cochlear implant system 610 includes a behind-the-ear sound processor 612 communicating, by way of a cable 614 and a headpiece 616, with a cochlear implant 618 connected to an electrode lead 620 with a plurality of electrodes including a probative (e.g., leading) electrode 622. Components of cochlear implant system 610 may correspond to similar components in other cochlear implant systems described herein and may operate accordingly. For example, under direction of a computing device 624, sound processor 612 may send commands to cochlear implant 618 (e.g., by way of cable 614 and headpiece 616) to direct cochlear implant 618 to detect an evoked response within cochlea 608 using probative electrode 622 on electrode lead 620. As with computing device 302 described above, computing device 624 may obtain an audiometric measurement by causing the evoked response to be detected by cochlear implant system 610 in conjunction with directing acoustic stimulation generator 514 to generate acoustic stimulation configured to propagate through sound propagation channel 516 provided by sound delivery apparatus 500 (i.e., through tubing 502 and ear tip 508).

As shown, permanent bend 520 angles tubing 502 toward pinna 602 so as to reduce an interaction of the surgeon with tubing 502. In other words, as shown, permanent bend 520 moves tubing 502 down out of the way (e.g., in any direction as the surgeon may desire) so that tubing 502 does not stick straight out of ear canal 604 as would be the case with a conventional sound delivery apparatus. At the same time, permanent bend 520 allows sound propagation channel 516 to remain unobstructed by keeping sound delivery apparatus 500 (i.e., tubing 502 and the internal portion of ear tip 508) from kinking.

Additionally, ear tip 508 may have other desirable characteristics that have not been conventionally available in intraoperative sound delivery apparatuses. For example, as shown, the external portion of ear tip 508 may be configured to interface with ear canal 604 of the patient so as to acoustically isolate interior 604-1 of ear canal 604 from exterior 604-2 of ear canal 604. In other words, ear tip 508 may be flexible to form a close, customized, fit within ear canal 604 such that sound propagation channel 516 is the only air channel by way of which sound may propagate between interior 604-1 and exterior 604-2. This close fit may make ear tip comfortable, ergonomic, easy to position, and, may allow for precise control (e.g., by computing device 624 and/or acoustic stimulation generator 514) of an amount, level, or degree of acoustic stimulation that is presented to the patient. In contrast, certain conventional ear tips designed for applications in which some leakage is tolerated or desirable rather than complete isolation (e.g., certain ear tips used for earphones, ear plugs, etc.) may be intentionally designed to allow at least some leakage (e.g., some form of sound propagation channel other than sound propagation channel 516) by way of which ambient sound may reach interior 604-1 of ear canal 604. While ear tip 508 is illustrated as being disposed relatively deep within ear canal 604, it will be understood that, in certain examples, ear tip 508 may be disposed right at the entrance to ear canal 604 or at any other suitable position with respect to ear canal 604.

Another desirable characteristic that may be provided by ear tip 508 in contrast to certain conventional ear tips is that ear tip 508 may be configured to be biocompatible and sterilizable for use by the patient within a sterile field associated with the surgical operation while the patient is undergoing the surgical operation. For example, in order to provide a high degree of isolation and stability (e.g., so as to not become dislodged), certain conventional intraoperative sound delivery apparatuses have used a compressible/decompressible foam material designed to be inserted into the ear canal in a compressed state and to then decompress within the ear canal to form a strong seal with a good degree of stability and isolation. However, due to a porous nature of such foam material, it may not be possible to achieve a suitable level of sterilization in such materials to be safely used near a sterile field of a surgery. For example, even if the ear canal is intended to remain outside of the sterile field associated with a surgical operation, a risk of fluids inadvertently leaking or other unexpected events may exist that could potentially cause the ear canal to come within the sterile field, thereby rendering any unsterilized materials (e.g., such as foam ear tips) potentially hazardous to the patient. Accordingly, it may be desirable for ear tip 508 to be constructed of a sterilizable (e.g., nonporous) material that is still flexible enough to provide a good isolation seal.

Figure 7:
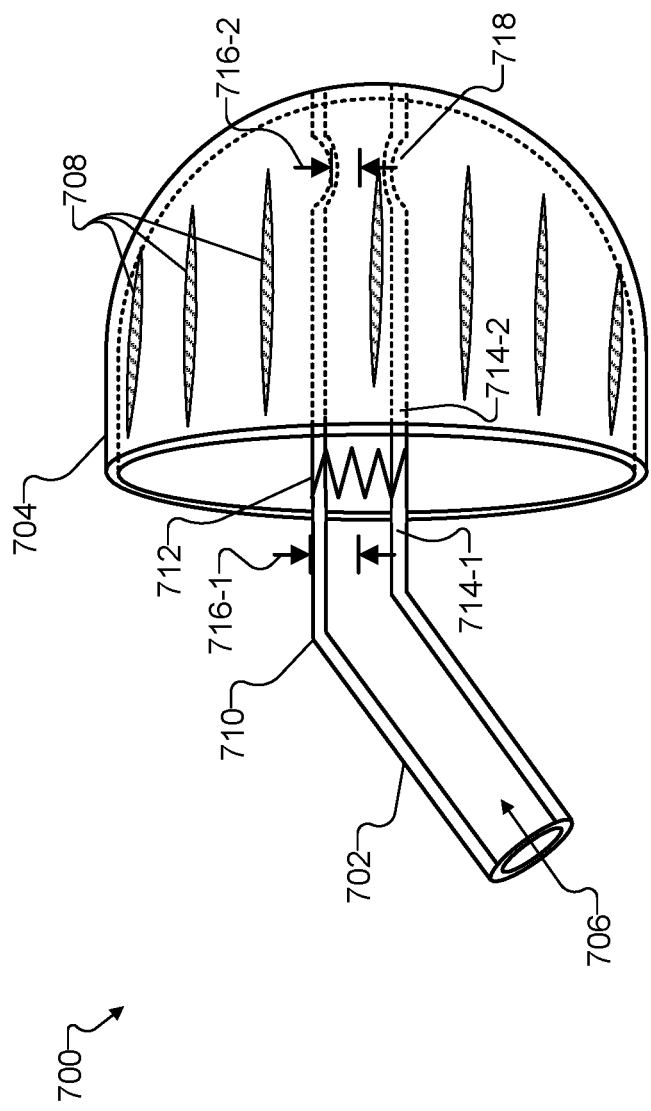
FIG. 7 illustrates an exemplary ear tip for use in certain implementations of sound delivery apparatuses for audiometric measurements according to principles described herein.

To this end, FIG. 7 illustrates an exemplary ear tip 700 for use in certain implementations of sound delivery apparatuses for audiometric measurements. For example, an ear tip having some or all of the features of ear tip 700 may implement ear tip 508 used in sound delivery apparatus 500 and intraoperative measurement system 600 described above. Specifically, for instance, if ear tip 700 implements ear tip 508, standard tubing (e.g., tubing in which the distal end does not include any permanent bend) may be used to implement tubing 502 in sound delivery apparatus 500. In other implementations, however (e.g., implementations using special tubing or a special coupling adapter), certain features of ear tip 700 may not be included within an implementation of ear tip 508. For example, in such implementations, ear tips having more conventional features described herein (e.g., lacking a permanent bend on the internal portion, including an external portion constructed of foam, etc.) may be employed.

As shown in FIG. 7, ear tip 700 may include an internal portion 702, an external portion 704, and a sound propagation channel 706 (e.g., or at least a first portion thereof). External portion 704 of ear tip 700 is implemented as a dome constructed of a flexible material. For example, a soft, compliant material such as silicone or another elastomeric material may be used to provide a comfortable, natural fit in the ear canal of the patient while also providing a good isolation seal between the interior and exterior of the ear canal and at least some physical stability to help prevent ear tip 700 from becoming dislodged. While the dome of external portion 704 is illustrated as being a circular dome in the example of ear tip 700, it will be understood that the dome may have different shapes (e.g., shapes configured to better contour to the ear canal or another portion of the ear) as may serve a particular implementation.

As illustrated, the dome of external portion 704 may include a plurality of rib features 708 disposed around the dome. Rib features 708 may be configured to run longitudinally with the ear canal when the dome interfaces with the ear canal of the patient. Accordingly, rib features 708 may provide structural support to the dome as the dome interfaces with (e.g., makes contact with so as to conform and contour to) the ear canal. For example, rib features 708 may provide structural support to help the dome retain its shape to some degree (e.g., to fully form a seal with the ear canal) even as the flexible material of the dome flexes in contact with the ear canal. Rib features 708 may be configured, distributed, disposed, placed, or otherwise implemented in any manner as may serve a particular implementation. For example, in some implementations, rib features 708 may be formed from the same material as the rest of the dome of external portion 704 and may be disposed on an interior of the dome. In other examples, rib features 708 may be disposed on an exterior of the dome and/or may be constructed of a different material from the rest of the dome (e.g., an elastomeric material with a durometer higher than the rest of the dome, etc.). Rib features 708 may be evenly spaced 360-degrees around the dome in some examples, while being unevenly distributed and/or distributed only on certain sides of the dome in other examples.

In the example of ear tip 700, internal portion 702 itself includes a permanent bend 710. Specifically, as shown, permanent bend 710 may be associated with a coupling between a distal end of a length of tubing such as tubing 502 (not explicitly shown) and internal portion 702 of ear tip 700 by being implemented on internal portion 702 of ear tip 700 near where internal portion 702 of ear tip 700 is configured to be coupled to the distal end of the tubing. As such, in examples where ear tip 700 is used, the distal end of the tubing may not include any permanent bend. In other words, ear tip 700 may be used with conventional tubing and may still provide benefits and advantages described herein.

While it may be desirable for permanent bend 710 to remain relatively stiff or inflexible so as to force sound propagation channel 706 and tubing attached to ear tip 700 to make an angled approach to the ear canal rather than a straight approach (i.e., rather than an approach at an angle substantially parallel to the ear canal), the opposite may be true for the part of internal portion 702 that connects to external portion 704. In other words, where internal portion 702 meets external portion 704, it may be desirable for internal portion 702 to be flexible so as to put as little strain as possible on the interface between external portion 704 and the ear canal while internal portion 702 and/or tubing connected thereto are bumped and jostled as audiometric measurements are being obtained (e.g., as surgery is being performed). To this end, ear tip 700 shows a division 712 between a first part 714-1 and a second part 714-2 of internal portion 702 of ear tip 700. First part 714-1 may be constructed of a first material having a first durometer and, as shown, may implement permanent bend 710 and be configured to couple to the distal end of the tubing. Conversely, second part 714-2 may be physically connected to external portion 704 and may be constructed of a second material having a second durometer less than (e.g., more flexible than) the first durometer. For example, second part 714-2 may be constructed from the same material as external portion 704, while first part 714-1 may be constructed from a stiffer material such as a higher durometer silicone, an overmolded thermoplastic, or the like.

In this way, permanent bend 710 and sound propagation channel 706 may be more likely to maintain their structural integrity (e.g., to avoid bending or kinking, etc.) while a degree of strain relief may be provided with respect to strain that movements to internal portion 702 pass on to external portion 704. Additionally, other strain relief features may be implemented to further invoke the same effect. For example, as shown, internal portion 702 of ear tip 700 may be implemented as a tubular element including a proximal end at which the distal end of the tubing is to be coupled (i.e., the end corresponding to part 714-1) and a distal end at which external portion 704 of ear tip 700 is coupled to internal portion 702 (i.e., the end corresponding to part 714-2). A first radius 716-1 may thus characterize the entirety of part 714-1 corresponding to the proximal end of the tubular element and, in some examples as described above, may be rigidly maintained by way of a relatively high durometer material. However, as shown, radius 716-1 at the proximal end of the tubular element may be greater than a second radius 716-2 of the tubular element characterizing a neck 718 of the tubular element disposed near the distal end of the tubular element (e.g., on part 714-2 near the coupling to external portion 704).

This is because neck 718 of the tubular element may be configured to provide strain relief for external portion 704 of ear tip 700 as external portion 704 interfaces with the ear canal of the patient and as internal portion 702 flexes in relation to external portion 704. In other words, with its smaller radius 716-2 and/or with the more flexible material from which part 714-2 is constructed, neck 718 may be configured to allow a relatively high degree of freedom for internal portion 702 to flex in any direction (e.g., up, down, left, right, etc.) while transferring a relatively small amount of strain to external portion 704 (e.g., which may be seated within or otherwise interfacing with the ear canal of the patient).

Figure 8A:
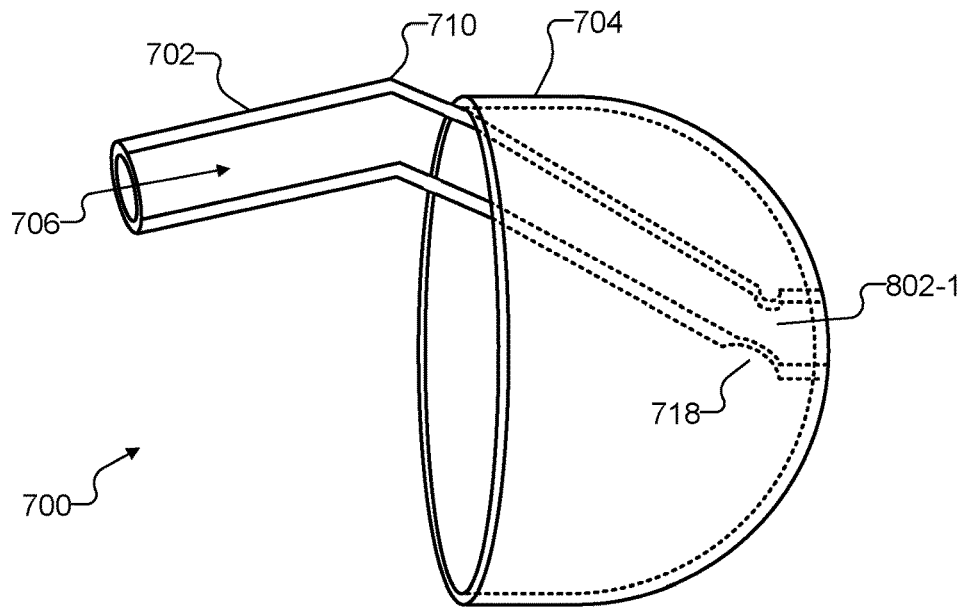
FIGS. 8A-8B illustrate a strain relief feature of the ear tip of FIG. 7 in operation according to principles described herein.
Figure 8B:
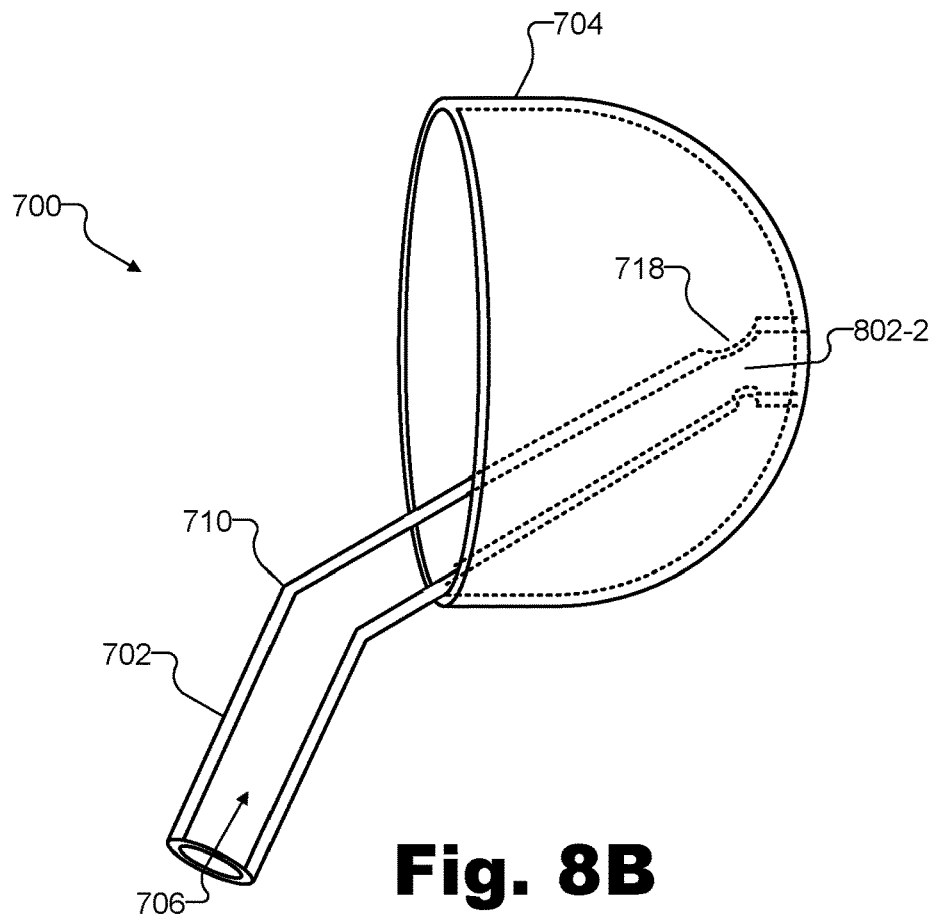

To illustrate, FIGS. 8A-8B show the strain relief features of ear tip 700 in operation. For example, in FIG. 8A, ear tip 700 is illustrated with a large degree of strain imposed on internal portion 702, causing internal portion 702 to flex to a large degree in an upward direction, while in FIG. 8B, a similarly large degree of strain is imposed on internal portion 702 to create a flexing in a downward direction. For example, the flexing of internal portion 702 illustrated in FIGS. 8A and/or 8B may be caused by tubing connected to ear tip 700 being bumped, jostled, or the like as audiometric measurements are obtained (e.g., as a surgical operation is performed), or by the tubing being arranged more permanently to stay out of the way (e.g., being taped down or the like). While only two directions of flexure are illustrated in FIGS. 8A and 8B (e.g., upward flexure in FIG. 8A and downward flexure in FIG. 8B), it will be understood that strain relief may be similarly provided for any angle of flexure 360 degrees around external portion 704 as may be imposed in various examples.

In spite of the flexing imposed in FIGS. 8A and/or 8B (or any other flexure as may be imposed in other examples), neck 718 is shown to absorb the flexing (i.e., to relieve the strain caused by the flexing) with minimal interference to external portion 704 as external portion 704 interfaces with the ear canal, as well as with a minimal effect on sound propagation channel 706. Specifically, as shown, sound propagation channel 706 remains open and unkinked through neck 718 in a section 802 labeled as 802-1 in FIG. 8A (i.e., where neck 718 relieves strain imposed in the upward direction) and labeled as 802-2 in FIG. 8B (i.e., where neck 718 relieves strain imposed in the downward direction). As described above, by using different materials to construct internal portion 702 (e.g., using a lower durometer material for neck 718 and the surrounding distal part of internal portion 702 than for permanent bend 710 and the surrounding proximal part of internal portion 702), strain relief provided by neck 718 may be enhanced and/or additional strain relief may be provided.

In FIGS. 7, 8A, and 8B, internal portion 702 of ear tip 700 has been illustrated as implementing permanent bend 710 to angle the tubing toward the pinna of the patient (e.g., to reduce an interaction that a surgeon performing a surgical operation may have with the tubing). It will be understood, however, that in certain examples, the permanent bend configured to angle the tubing toward the pinna of the patient may be implemented by other components of the sound delivery apparatus associated with the coupling between the tubing and the ear tip, rather than on the ear tip itself.

As one example, for instance, the permanent bend may be associated with the coupling between the distal end of the tubing and the internal portion of the ear tip by being implemented on a coupling adapter configured to be disposed between the distal end of the tubing and the internal portion of the ear tip so as to couple the distal end of the tubing to the internal portion of the ear tip. As such, in this example, neither the internal portion of the ear tip nor the distal end of the tubing may include any permanent bend (e.g., straight tubing and a straight ear tip such as a standard ear tip and standard tubing may be employed together with the coupling adapter to implement the sound delivery apparatus).

Figure 9:
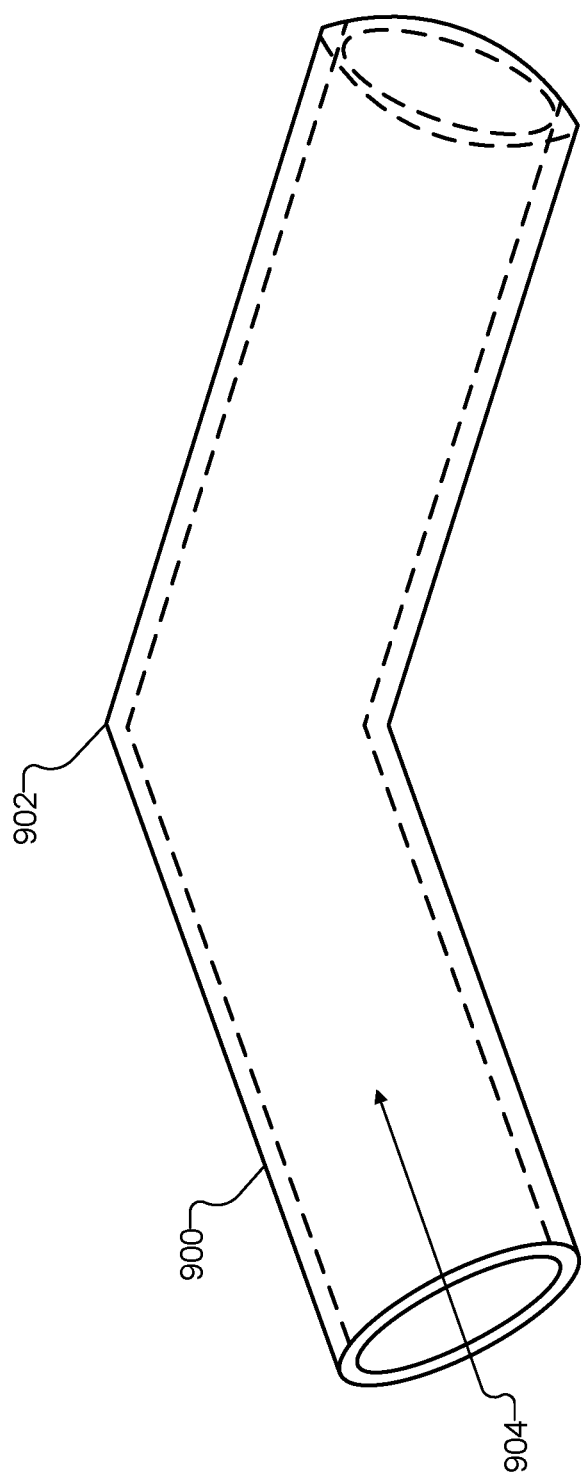
FIG. 9 illustrates an exemplary coupling adapter for use in certain implementations of sound delivery apparatuses for audiometric measurements according to principles described herein.

To illustrate, FIG. 9 shows an exemplary coupling adapter 900 for use in certain implementations of a sound delivery apparatus for audiometric measurements such as sound delivery apparatus 500. Specifically, coupling adapter may be configured to be connected between the distal end of the tubing and the proximal end of the internal portion of the ear tip to thereby insert a permanent bend 902 into the coupling between them. In this way, as shown in FIG. 9, a third portion 904 of a sound propagation channel may be implemented to complete the sound propagation channel formed by the tubing (providing the first portion of the channel) and the internal portion of the ear tip (providing the second portion of the channel), and third portion 904 may include the permanent bend to provide the benefits described herein.

As another example, the permanent bend may be associated with the coupling between the distal end of the tubing and the internal portion of the ear tip by being implemented on the distal end of the tubing near where the distal end of the tubing is configured to be coupled to the internal portion of the ear tip. As such, in this example, no coupling adapter may be employed and the internal portion of the ear tip may not include any permanent bend (e.g., a straight ear tip such as a standard ear tip may be employed together with the tubing to implement the sound delivery apparatus).

Figure 10:
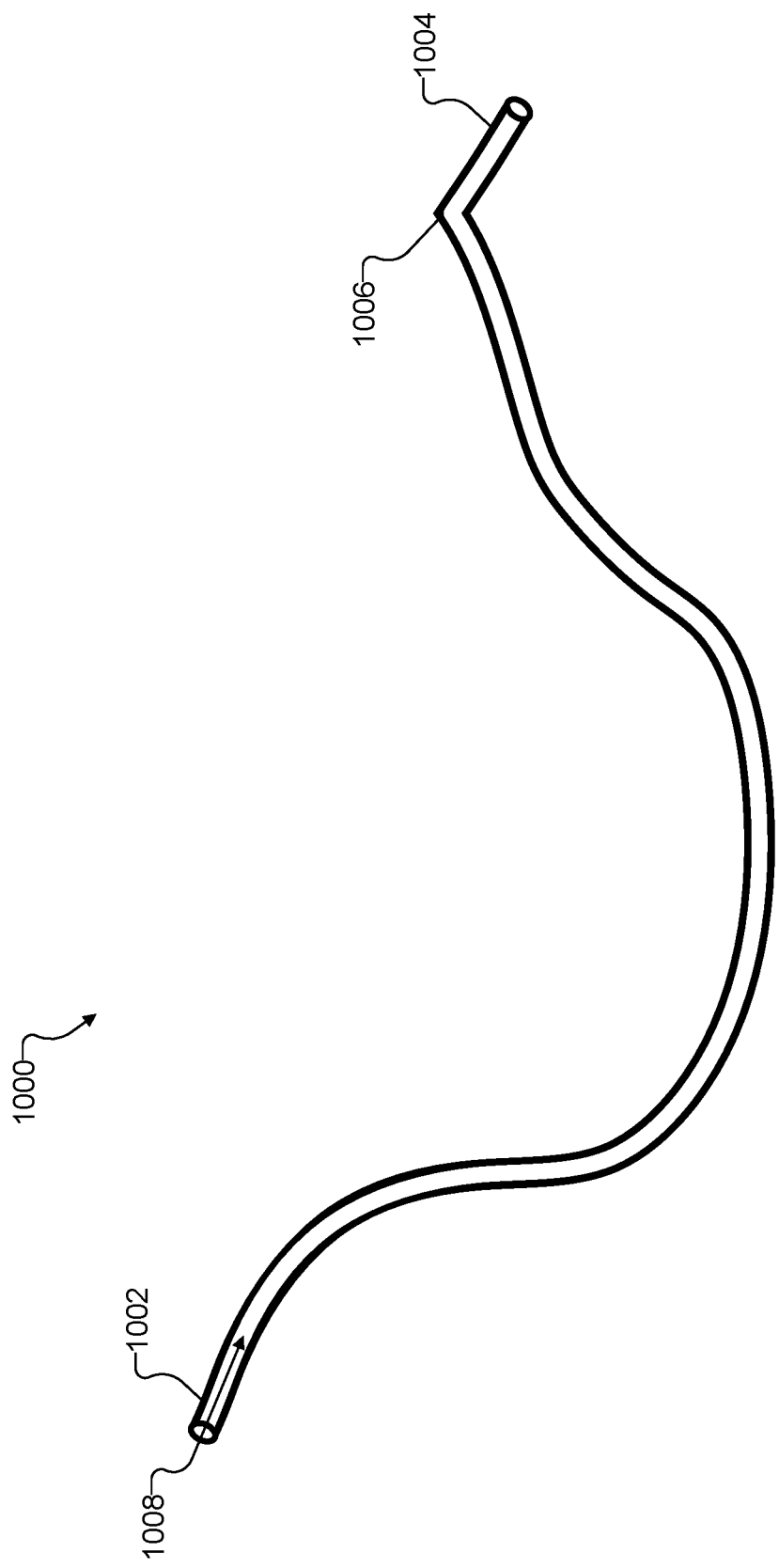
FIG. 10 illustrates an exemplary length of tubing for use in certain implementations of sound delivery apparatuses for audiometric measurements according to principles described herein.

To illustrate, FIG. 10 shows an exemplary length of tubing 1000 for use in certain implementations of sound delivery apparatuses for audiometric measurements such as sound delivery apparatus 500. As shown, tubing 1000 includes a proximal end 1002, a distal end 1004, and a permanent bend 1006. Additionally, tubing 1000 is configured to provide a first portion of a sound propagation channel 1008 for carrying acoustic stimulation generated by an acoustic stimulation generator coupled to tubing 1000 at proximal end 1002. Any suitable type of tubing described herein may be used to implement tubing 1000 as may serve a particular implementation, and tubing 1000 may include various features (e.g., biocompatibility, sterilizability, etc.) that may allow tubing 1000 to be employed in particular applications such as intraoperative surgical scenarios.

As mentioned above, certain audiometric measurements may be most accurate, effective, and/or useful when there is a high degree of precision associated with the acoustic stimulation delivered to the patient. For example, audiometric measurements may be most accurate, effective, and/or useful when precisely known and/or controlled levels (e.g., loudness levels, sound pressure levels, etc.) of acoustic stimulation are delivered to the ear canal of the patient in connection with the audiometric measurements being obtained. Accordingly, it may be advantageous in certain examples for sound delivery apparatuses to facilitate the monitoring of the acoustic stimulation used to obtain an audiometric measurement within the ear canal of the patient.

To this end, various implementations of sound delivery apparatus 500 (e.g., including implementations that include an ear tip such as ear tip 700) may include features to facilitate such monitoring. Specifically, for example, the internal portion of an ear tip such as ear tip 700 may be constructed to include a lumen configured to facilitate monitoring, within the ear canal of the patient, the acoustic stimulation used to obtain the audiometric measurement. The lumen may be physically separated from the sound propagation channel throughout the internal portion of the ear tip. In other words, the lumen may provide a second, separate channel (e.g., along with the sound propagation channel) between an isolated portion of the ear canal of the patient and the outside world external to the ear canal.

The lumen may facilitate monitoring the acoustic stimulation in any suitable way. For instance, in certain implementations, the lumen may be configured to allow a probe microphone (e.g., a small microphone at the end of a thin wire) to be inserted into the lumen (e.g., to be inserted all the way in such that the probe microphone is disposed at or near the distal tip of the internal portion of the ear tip). In this way, the probe microphone may monitor the acoustic stimulation used to obtain the audiometric measurement within the isolated portion of the ear canal while the ear tip is disposed at the ear canal. For example, the probe microphone may be used as one or more audiometric measurements are being obtained (e.g., as tests are being run), prior to actual audiometric measurement being obtained (e.g., during a preliminary calibration operation), or at any other suitable time.

In the same or other implementations, the lumen may be configured to allow sound waves to exit the isolated portion of the ear canal to a probe microphone that is not inserted all the way into the lumen or to another type of microphone disposed at a proximal end of the lumen. For example, while the sound propagation channel may act as a channel for acoustic stimulation to be delivered to the ear canal, the lumen may act as a channel for delivering sound waves associated with the acoustic stimulation from the ear canal for monitoring and feedback purposes.

In some examples, the lumen may extend not only through the internal portion of the ear tip, but may also extend through the tubing of an implementation of sound delivery apparatus 500 (e.g., in a similar way as the sound propagation channel). In other examples, however, the lumen may not extend throughout the entirety of the tubing, but may, for example, only extend throughout the internal portion of the ear tip and may have a proximal end on the internal portion of the ear tip that may serve as an interface for inserting the probe microphone, monitoring sound exiting the lumen, or the like.

To illustrate how certain implementations of sound delivery apparatus 500 may facilitate monitoring acoustic stimulation within an ear canal of a patient, FIGS. 11A through 11D illustrate cross sectional views of exemplary implementations of ear tip 700 that are configured to facilitate monitoring acoustic stimulation used to obtain an audiometric measurement with respect to the patient. More particularly, FIG. 11A illustrates an exemplary cross section view 1100-1 taken perpendicular to a longitudinal axis of a first implementation of internal portion 702 of ear tip 700 (labeled as internal portion 702-1); FIG. 11B illustrates an exemplary cross section view of ear tip 700 taken parallel to the longitudinal axis of internal portion 702-1; FIG. 11C illustrates an exemplary cross section view 1100-2 taken perpendicular to a longitudinal axis of a second implementation of internal portion 702 of ear tip 700 (labeled as internal portion 702-2); and FIG. 11D illustrates an exemplary cross section view of ear tip 700 taken parallel to the longitudinal axis of internal portion 702-2.

As shown, and as described above, both implementations of internal portion 702 of ear tip 700 (i.e., internal portions 702-1 and 702-2) may be implemented as tubular elements. Along these respective tubular elements, exemplary lumens may be implemented in different ways. Specifically, as illustrated in FIGS. 11A and 11B, a lumen 1102 may be implemented along an outer portion of the tubular element implementing internal portion 702-1. Conversely, as an alternative illustrated in FIGS. 11C and 11D, a lumen 1104 may be implemented along an inner portion of the tubular element implementing internal portion 702-2. As described above, regardless of whether the lumen is implemented along the outer portion (e.g., such as with lumen 1102) or the inner portion (e.g., such as with lumen 1104), the lumen may be physically separated from sound propagation channel 706 (e.g., by walls of the tubular element). Accordingly, as further described above, either of lumens 1102 or 1104, or another lumen suitably implemented in accordance with principles described herein, may facilitate monitoring acoustic stimulation used to obtain audiometric measurements in any of the ways described herein or in any other suitable manner. For example, a probe microphone may be inserted to extend all the way through lumens 1102 and/or 1104, lumens 1102 and/or 1104 may serve as a sound propagation channel to deliver sound from the ear canal to an external microphone, or the like.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:
a length of tubing configured to physically couple, at a proximal end of the tubing, to an acoustic stimulation generator configured to generate sound waves representative of acoustic stimulation used to obtain an audiometric measurement with respect to a patient, the tubing providing a first portion of a sound propagation channel from the acoustic stimulation generator to an ear canal of the patient;
an ear tip configured to be disposed at the ear canal of the patient, the ear tip including:
 an external portion configured to interface with the ear canal of the patient, the external portion implemented as a dome constructed of a flexible material, and
 an internal portion implemented as a tubular element and including:
  a proximal end having a first radius and configured to be coupled to a distal end of the tubing to provide a second portion of the sound propagation channel,
  a distal end coupled to the external portion of the ear tip, the distal end having a second radius, and
  a neck disposed near the distal end of the tubular element within the dome of the external portion and configured to provide, by having a third radius smaller than the first radius and the second radius, strain relief for the external portion of the ear tip as the external portion interfaces with the ear canal and the internal portion flexes in relation to the external portion, wherein the neck is configured such that the proximal end of the internal portion is pivotable in relation to the distal end of the internal portion; and
a permanent bend associated with a coupling between a distal end of the tubing and the proximal end of the internal portion of the ear tip, the permanent bend configured to be disposed immediately outside the ear canal of the patient so as to angle the tubing toward a pinna of the patient without obstructing the sound propagation channel when the ear tip is disposed at the ear canal and coupled to the distal end of the tubing.

2. The apparatus of claim 1, wherein:
the audiometric measurement is an intraoperative audiometric measurement performed with respect to the patient as the patient is undergoing a surgical operation associated with a cochlea of the patient; and
the permanent bend is configured to angle the tubing toward the pinna as the patient is undergoing the surgical operation so as to reduce an interaction that a surgeon performing the surgical operation has with the tubing.

3. The apparatus of claim 1, wherein:
the audiometric measurement is an intraoperative audiometric measurement performed with respect to the patient as the patient is undergoing a surgical operation associated with a cochlea of the patient; and
the ear tip is configured to be biocompatible and sterilizable for use by the patient within a sterile field associated with the surgical operation while the patient is undergoing the surgical operation.

4. The apparatus of claim 1, wherein:
the permanent bend is associated with the coupling between the distal end of the tubing and the proximal end of the internal portion of the ear tip by being implemented near the proximal end of the internal portion of the ear tip; and the distal end of the tubing does not include any permanent bend.

5. The apparatus of claim 4, wherein:
a first part of the internal portion of the ear tip is constructed of a first material having a first durometer, the first part implementing the permanent bend and being configured to couple to the distal end of the tubing; and
a second part of the internal portion of the ear tip is constructed of a second material having a second durometer less than the first durometer.

6. The apparatus of claim 1, wherein:
the permanent bend is associated with the coupling between the distal end of the tubing and the proximal end of the internal portion of the ear tip by being implemented on a coupling adapter configured to be disposed between the distal end of the tubing and the proximal end of the internal portion of the ear tip so as to couple the distal end of the tubing to the proximal end of the internal portion of the ear tip; and
neither the internal portion of the ear tip nor the distal end of the tubing includes any permanent bend.

7. The apparatus of claim 1, wherein:
the permanent bend is associated with the coupling between the distal end of the tubing and the proximal end of the internal portion of the ear tip by being implemented on the distal end of the tubing near where the distal end of the tubing is configured to be coupled to the proximal end of the internal portion of the ear tip; and
the internal portion of the ear tip does not include any permanent bend.

8. The apparatus of claim 1, wherein the external portion of the ear tip is configured to interface with the ear canal of the patient so as to acoustically isolate an interior of the ear canal from an exterior of the ear canal.

9. The apparatus of claim 1, wherein the dome includes a plurality of rib features disposed around the dome and configured to
run longitudinally with the ear canal when the dome interfaces with the ear canal of the patient, and
provide structural support to the dome as the dome interfaces with the ear canal and the flexible material flexes in contact with the ear canal.

10. The apparatus of claim 1, wherein the internal portion of the ear tip includes a lumen configured to facilitate monitoring, within the ear canal of the patient, the acoustic stimulation used to obtain the audiometric measurement, the lumen physically separated from the sound propagation channel throughout the internal portion of the ear tip.

11. The apparatus of claim 10, wherein the lumen is implemented along an outer portion of the tubular element implementing the internal portion.

12. The apparatus of claim 10, wherein the lumen is implemented along an inner portion of the tubular element implementing the internal portion.

13. An apparatus comprising:
an ear tip configured to be disposed at an ear canal of a patient, the ear tip including
an external portion configured to interface with the ear canal of the patient, the external portion implemented as a dome constructed of a flexible material, and
an internal portion implemented as a tubular element and including:
a proximal end having a first radius and configured to be coupled to a distal end of a length of tubing to provide a second portion of a sound propagation channel from an acoustic stimulation generator to the ear canal of the patient, the acoustic stimulation generator configured to generate sound waves representative of acoustic stimulation used to obtain an audiometric measurement with respect to the patient, and the tubing configured to physically couple to the acoustic stimulation generator at a proximal end of the tubing and to provide a first portion of the sound propagation channel,
a distal end coupled to the external portion of the ear tip, the distal end having a second radius, and
a neck disposed near the distal end of the tubular element within the dome of the external portion and configured to provide, by having a third radius smaller than the first radius and the second radius, strain relief for the external portion of the ear tip as the external portion interfaces with the ear canal and the internal portion flexes in relation to the external portion, wherein the neck is configured such that the proximal end of the internal portion is pivotable in relation to the distal end of the internal portion; and
a permanent bend implemented within the internal portion of the ear tip, the permanent bend configured to be disposed immediately outside the ear canal of the patient so as to angle the tubing toward a pinna of the patient without obstructing the sound propagation channel when the ear tip is disposed at the ear canal and coupled to the distal end of the tubing.

14. The apparatus of claim 13, wherein:
a first part of the internal portion of the ear tip is constructed of a first material having a first durometer, the first part implementing the permanent bend and being configured to couple to the distal end of the tubing; and
a second part of the internal portion of the ear tip is constructed of a second material having a second durometer less than the first durometer.

15. The apparatus of claim 13, wherein the dome includes a plurality of rib features disposed around the dome and configured to
run longitudinally with the ear canal when the dome interfaces with the ear canal of the patient, and
provide structural support to the dome as the dome interfaces with the ear canal and the flexible material flexes in contact with the ear canal.

16. An intraoperative measurement system comprising:
a probative electrode disposed on an electrode lead included within a cochlear implant system, the probative electrode configured to detect, while the probative electrode is positioned at a particular location within a cochlea of a patient who is undergoing a surgical operation associated with the cochlea, an evoked response that occurs in response to acoustic stimulation applied to the patient to obtain an intraoperative audiometric measurement with respect to the patient;
an acoustic stimulation generator configured to generate sound waves representative of the acoustic stimulation;
a length of tubing configured to physically couple, at a proximal end of the tubing, to the acoustic stimulation generator, the tubing providing a first portion of a sound propagation channel from the acoustic stimulation generator to an ear canal of the patient;
an ear tip configured to be disposed at the ear canal of the patient while the patient is undergoing the surgical operation, the ear tip including an external portion configured to interface with the ear canal of the patient, the external portion implemented as a dome constructed of a flexible material, and an internal portion implemented as a tubular element and including:

a proximal end having a first radius and configured to be coupled to a distal end of the tubing to provide a second portion of the sound propagation channel, a distal end coupled to the external portion of the ear tip, the distal end having a second radius, and a neck disposed near the distal end of the tubular element within the dome of the external portion and configured to provide, by having a third radius smaller than the first radius and the second radius, strain relief for the external portion of the ear tip as the external portion interfaces with the ear canal and the internal portion flexes in relation to the external portion, wherein the neck is configured such that the proximal end of the internal portion is pivotable in relation to the distal end of the internal portion; and a permanent bend associated with a coupling between a distal end of the tubing and the proximal end of the internal portion of the ear tip, the permanent bend configured to be disposed immediately outside the ear canal of the patient so as to angle the tubing toward a pinna of the patient without obstructing the sound propagation channel when the ear tip is disposed at the ear canal and coupled to the distal end of the tubing as the patient is undergoing the surgical operation.

17. The intraoperative measurement system of claim 16, wherein:

the permanent bend is associated with the coupling between the distal end of the tubing and the proximal end of the internal portion of the ear tip by being implemented near the proximal end of the internal portion of the ear tip; and the distal end of the tubing does not include any permanent bend.

18. The intraoperative measurement system of claim 16, wherein:

the permanent bend is associated with the coupling between the distal end of the tubing and the proximal end of the internal portion of the ear tip by being implemented on a coupling adapter configured to be disposed between the distal end of the tubing and the proximal end of the internal portion of the ear tip so as to couple the distal end of the tubing to the proximal end of the internal portion of the ear tip; and neither the internal portion of the ear tip nor the distal end of the tubing includes any permanent bend.

19. The intraoperative measurement system of claim 16, wherein:

the permanent bend is associated with the coupling between the distal end of the tubing and the proximal end of the internal portion of the ear tip by being implemented on the distal end of the tubing near where the distal end of the tubing is configured to be coupled to the proximal end of the internal portion of the ear tip; and the internal portion of the ear tip does not include any permanent bend.

20. The intraoperative measurement system of claim 16, wherein:

the internal portion of the ear tip includes a lumen configured to facilitate monitoring, within the ear canal of the patient, the acoustic stimulation used to obtain the audiometric measurement, the lumen physically separated from the sound propagation channel throughout the internal portion of the ear tip; and the intraoperative measurement system further comprises a probe microphone configured to be inserted into the lumen to thereby monitor the acoustic stimulation used to obtain the audiometric measurement within the ear canal of the patient.

* * * * *